(12) United States Patent
Frederik et al.

(10) Patent No.: US 7,413,872 B2
(45) Date of Patent: Aug. 19, 2008

(54) DEVICE FOR PREPARING SPECIMENS FOR A CRYO-ELECTRON MICROSCOPE

(75) Inventors: Peter M. Frederik, Maastricht (NL); Paul H. H. Bomans, Meeuwen-Gruitrode (BE); Paul F. J. Laeven, Vijlen (NL); Franciscus J. T. Nijpels, Maastricht (NL)

(73) Assignee: Universiteit Maastricht, Maastricht (NL)

( * ) Notice: Subject to any disclaimer, the term of this patent is extended or adjusted under 35 U.S.C. 154(b) by 632 days.

(21) Appl. No.: 10/472,346

(22) PCT Filed: Mar. 22, 2002

(86) PCT No.: PCT/NL02/00189

§ 371 (c)(1), (2), (4) Date: Mar. 8, 2004

(87) PCT Pub. No.: WO02/077612

PCT Pub. Date: Oct. 3, 2002

(65) Prior Publication Data

US 2004/0157284 A1 Aug. 12, 2004

(30) Foreign Application Priority Data

Mar. 22, 2001 (NL) .................................. 1017669

(51) Int. Cl.
*G01N 1/30* (2006.01)
(52) U.S. Cl. ..................... 435/67; 435/287.1; 435/40.5; 422/99; 422/104
(58) Field of Classification Search ................ 436/174; 435/40.5, 287.7; 30/165; 422/67
See application file for complete search history.

(56) References Cited

U.S. PATENT DOCUMENTS

| 2,680,371 A | 6/1954 | Donath ........................... 73/17 |
| 4,753,887 A | 6/1988 | Bellare et al. ................ 435/287 |

OTHER PUBLICATIONS

Trachtenberg, S. "A Fast-Freezing Device with a Retractable Environmental Chamber, Suitable for Kinetic Cryo-Electron Microscopy Studies", Journal of Structural Biology, 1998, Academic Press, 123, pp. 45-55.*
"A Fast-Freezing Device with a Retractable Environmental Chamber, Suitable for Kinetic Cryo-Electron Microscopy Studies", by S. Trachtenberg, Journal of Structural Biology, vol. 123, 1998, pp. 45-55.
"Particle-surface interaction in thin vitrified films for cry-electron microscopy", by M. Cyrklaff et al., Journal of Microscopy, vol. 175, No. 2, Aug. 1994 pp. 135-142.
"Cryoplunge", retrieved from the Internet on Jul. 2002, http://www.gatan.com/pdf/Cryoplunge.pdf.

* cited by examiner

*Primary Examiner*—Jill Warden
*Assistant Examiner*—Imran Akram
(74) *Attorney, Agent, or Firm*—Steven M. Koehler; Westman, Champlin & Kelly, P.A.

(57) ABSTRACT

The invention relates to a device for preparing specimens for a cryo-electron microscope, comprising an environmental chamber, a holder for a sample or a carrier, and at least one blotting element to which a medium for absorbing liquid is or can be attached, both disposed in the environmental chamber, and a cooling medium for cooling down said sample. The said blotting element can be moved towards the sample or carrier in a controlled manner.

22 Claims, 3 Drawing Sheets

DEVICE FOR PREPARING SPECIMENS FOR A CRYO-ELECTRON MICROSCOPE

CROSS-REFERENCE TO RELATED APPLICATION

This Application is a Section 371 National Stage Application of International Application No. PCT/NL02/00189, filed Mar. 22, 2002 and published as WO 02/077612 on Oct. 3, 2002 in English.

BACKGROUND OF THE INVENTION

The invention relates to a device for preparing specimens for a cryo-electron microscope, comprising an environmental chamber, a holder for a sample or a carrier, and at least one blotting element to which a medium for absorbing liquid is or can be attached, both the holder and the blotting element(s) being disposed in the environmental chamber, and a cooling medium, preferably a container for a fluid, for cooling down the sample.

Besides the scanning electron microscope (SEM), wherein a scanning electron beam is used mainly for studying surfaces, various types of transmission electron microscopes (TEM) are used. With several of such microscopes, samples, for example a biopt or a cell suspension, are prepared by fixing and de-watering. After embedding a sample in a resin, an ultra-thin section (for example of 50 nm) can be cut, which is subsequently dyed and exposed to an electron beam.

In cryo-electron microscopy it is generally preferred to employ a so-called grid. For instance, a grid comprising hexagonal openings having a diameter of a few dozen microns is immersed in a suspension of particles to be examined, such as protein molecules or cells. Following that, the excess suspension is removed by "blotting", i.e. by pressing blotting paper or another medium that readily absorbs liquid against the grid on one side or on both sides thereof. As a result of blotting, the thickness of the film that is present in the openings of the grid is reduced, for example from 3-4 μm to 100 nm. In a film of such minimal thickness, an area which is even thinner develops in the centre of the film under the influence of the London/van der Waals attraction of the air/fluid boundary layers, which area slowly expands in outward direction, that is, in the direction of the edge of the respective opening in the grid. During this process, which is also referred to as draining, the suspended particles are trapped between the fluid surfaces. As a next step, the sample is cooled down very quickly, so that the fluid becomes vitreous. The specimen thus prepared can be examined in a cryo-electron microscope at a low temperature (for example minus 170° C.) and be photographed without any additional operations being required.

A device for preparing specimens for a cryo-electron microscope is known, for example, from S. Trachtenberg, "A Fast-Freezing Device with a Retractable Environmental Chamber, Suitable for Kinetic Cryo-Electron Microscopy Studies", Journal of Structural Biology 123, 45-55 (1998). Said publication describes a device which comprises an environmental chamber having transparent polycarbonate walls. Disposed under said chamber is a bath of liquid ethane. The temperature and the (high) air humidity in the chamber are controlled by means of heating elements and an ultrasonic air humidifier. After a grid has been provided with a sample, blotting takes place either manually or automatically by means of an independent unit. Then a valve present in the bottom of the chamber is opened and the grid falls into the ethane at high speed, so that the sample cools down very quickly, i.e. vitrifies. Following that, the chamber is moved up and the specimen is ready.

A similar device is known from a PhD thesis by J. Bednar, "Cryo-Electron Microscopy of DNA and Chromatin", Lausanne 1995. This thesis describes (especially in Chapter 7 in conjunction with FIG. 7.1) a "plunger ... (which) consists of stand., humid chamber, tweezers holder, and blotting pad as major parts". The blotting pad is connected with a driving magnet via a photographic wire remote shutter.

Such arrangements and method suit the perception that the specimen is sensitive to changes in the temperature and air humidity levels until the moment of freezing. It has become apparent, however, that the existing equipment is insufficiently capable of preparing large numbers of specimens in a reproducible manner.

SUMMARY OF THE INVENTION

The object of the present invention is to provide an improved device of the type described in the first paragraph, by means of which specimens can be prepared in a more easily reproducible manner.

In order to accomplish that objective, the device includes a blotting element that can be moved towards the sample or carrier in a controlled manner. It is preferred that the pressure and/or the speed with which the blotting element(s) is (are) pressed against respectively moved towards the sample or carrier are adjustable.

The reproducibility of the specimen preparation process was found to depend much stronger on blotting than had been assumed so far. Moreover, the preparation of specimens can take place in a (relatively) simple and largely automated manner when using the device according to the invention.

In another embodiment, the blotting element(s) are operatively connected to a driving mechanism (control unit), which can include a personal computer (PC), which is arranged to control the movements of the blotting element(s) so as to blot the sample or carrier one or more times at a predetermined pressure and, in a further embodiment also to control the speed of at least some of the movements of the blotting element(s).

The invention furthermore relates to a method for preparing a specimen by using the device described herein, wherein the sample or the carrier is being blotted simultaneously from either side of the sample or carrier. Thus, the forces exerted on the sample or carrier by the blotting elements more balanced and hence more controllable.

Within the framework of the invention, the term "carrier" comprises any device suitable for carrying a sample. Examples of such devices comprise relatively simple metal pins, to which a sample or a suspension containing a sample will stick, quantifoils, and the above-mentioned grids. Grids can be provided with holes of various shapes, e.g. hexagonal, round, square or the like, and/or can be provided on one or both sides with a support film provided with such holes.

The phrase "in a controlled manner" means that at least some of the blotting parameters, for example, at least the pressure exerted by the blotting elements, can be adjusted and/or regulated before and/or during blotting.

BRIEF DESCRIPTION OF THE DRAWINGS

The invention will now be explained in more detail with reference to the appended figures, which schematically show an exemplary embodiment of the device according to the present invention.

DETAILED DESCRIPTION OF THE ILLUSTRATIVE EMBODIMENTS

Figure 1:
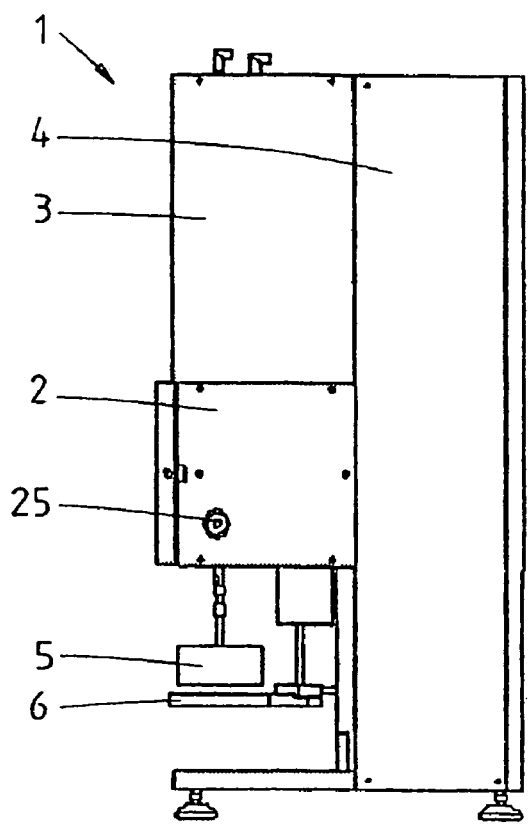
FIGS. 1 and 2 are a front view and a side elevation, respectively, of a device for preparing specimens for a cryo-electron microscope.
Figure 2:
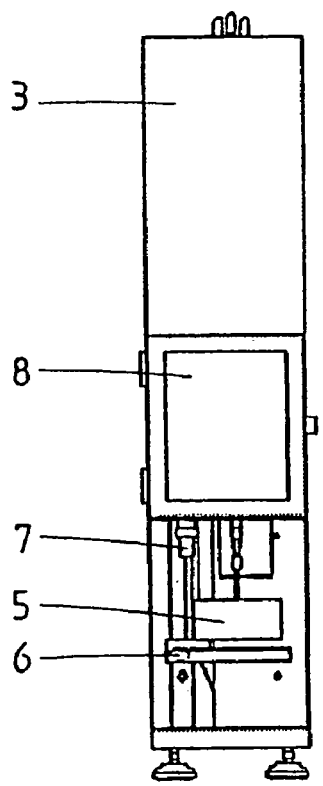

FIGS. 1 and 2 show a device 1 for preparing specimens for a cryo-electron microscope, comprising an environmental chamber 2, a front compartment 3, in which the actuators for components in the environmental chamber 2 that are yet to be discussed are accommodated, and a rear compartment 4, in which an electronic and/or pneumatic control unit 29 (FIG. 3) for the aforesaid actuators or means for communication with an external control unit may be present.

Disposed under the environmental chamber 2 is a vessel 5, known in itself, comprising a central cavity for receiving a cooling medium by means of which a specimen can be vitrified, for example liquid ethane. The vessel 5 may furthermore comprise an annular channel surrounding the central cavity, for example, into which a second cooling medium, such as liquid nitrogen, can be introduced. Said medium can be used for cooling the ethane and/or for temporary storage of specimens that are finished. Vessel 5 can be moved upwards and downwards by means of a table 6 and an associated actuator (not shown). The interior of environmental chamber 2 is accessible through a door 8, which is fitted with a window.

Figure 3:
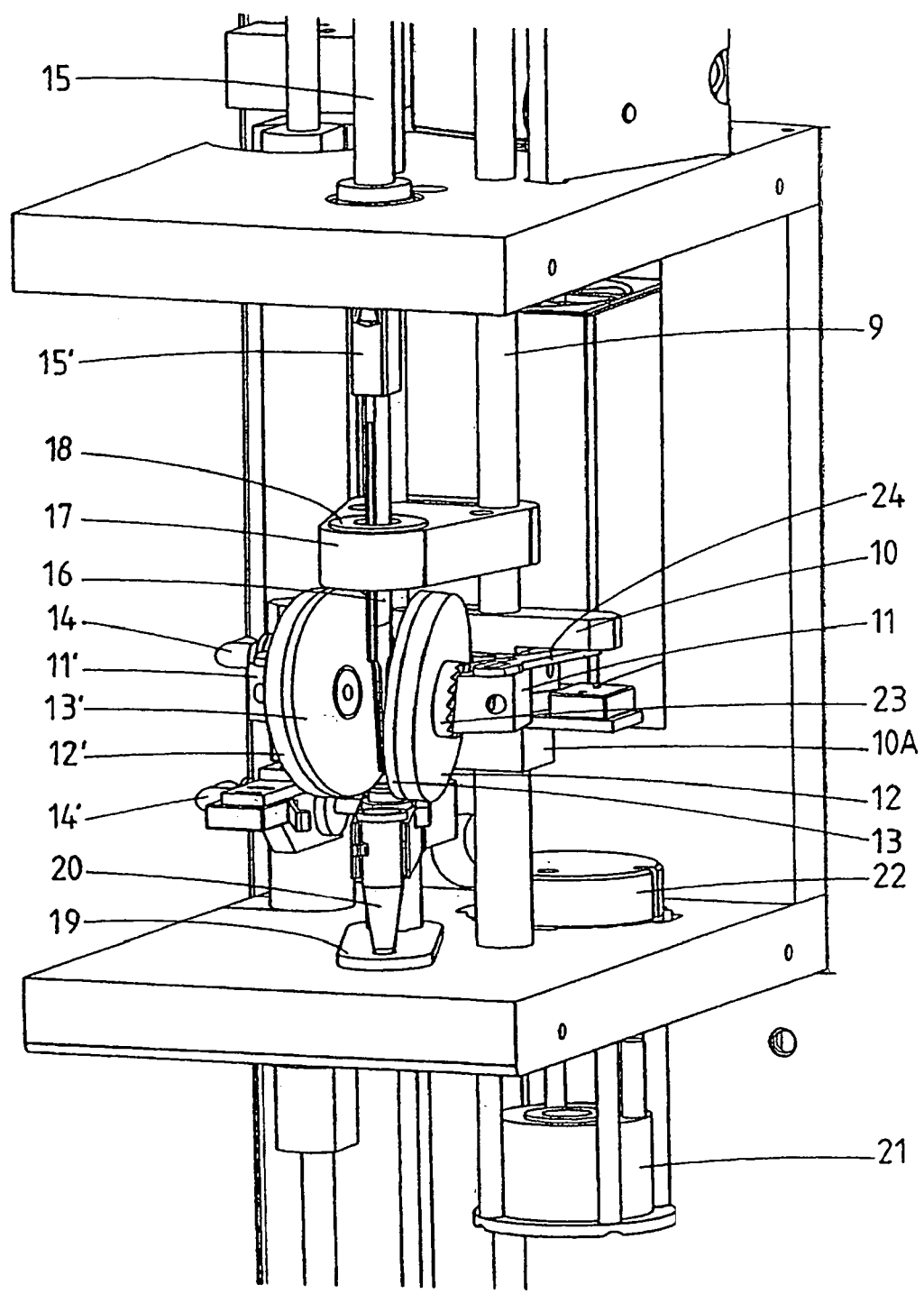
FIG. 3 is a perspective view of part of the interior of the environmental chamber of the device according to FIGS. 1 and 2.
Figure 4:
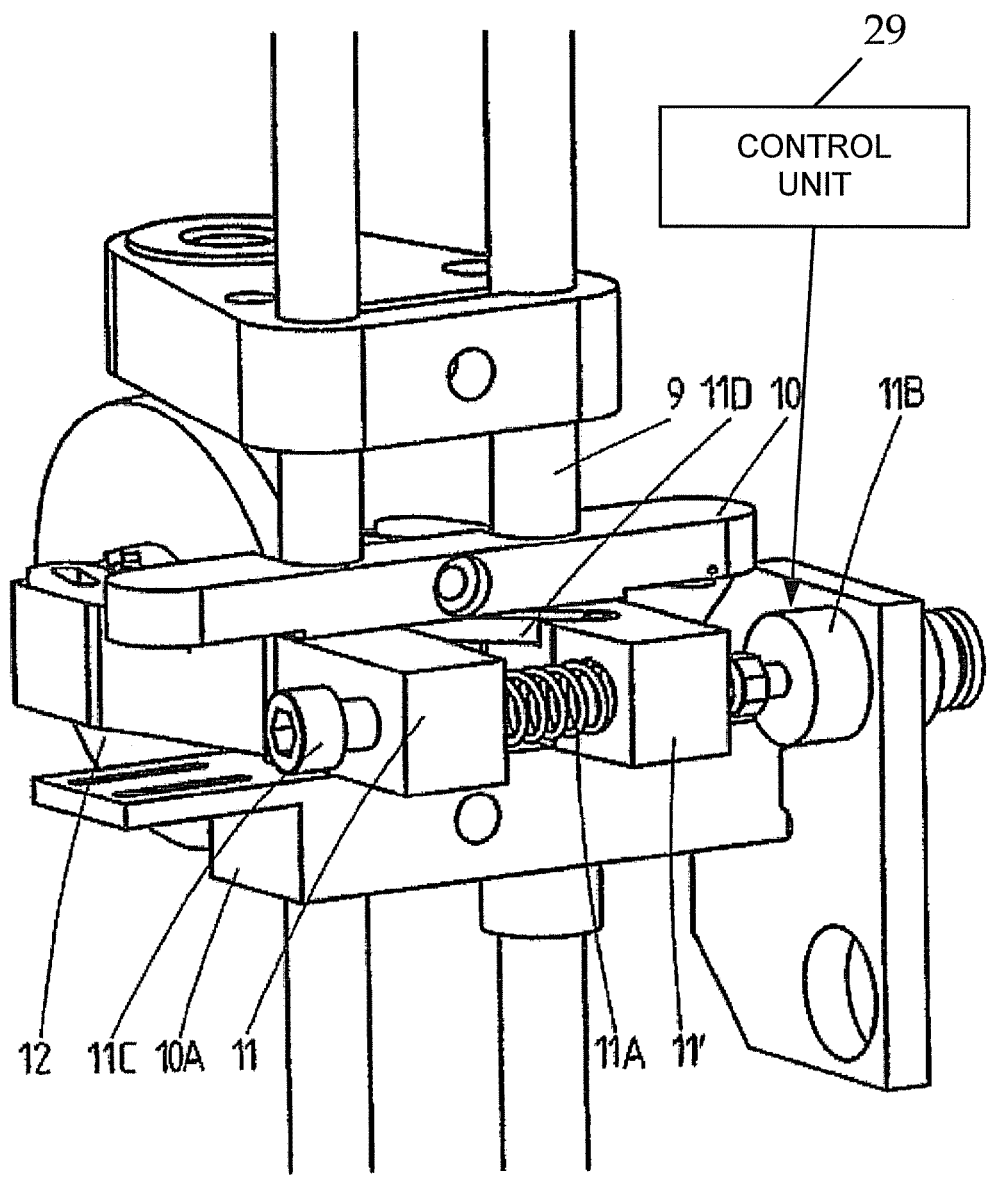
FIG. 4 is a perspective rear view of the blotting mechanism in FIG. 3.

The interior of environmental chamber 2 is shown in FIGS. 3 and 4, since the side walls and the door 8 have been left out in these Figures. Environmental chamber 2 comprises two parallel tubes 9, which function to support part of the other components in environmental chamber 2. Connected to tubes 9 are a cross beam 10 and a subframe 10A, which in turn provide support for two pivotable arms 11, 11'. Circular blotting elements 12, 12' are mounted rotatably and obliquely on the ends of said arms 11, 11'. Each of said blotting elements 12, 12' comprises a pad or cushion 13, 13', to which a blotting paper or other liquid-absorbing medium can be attached. Each of the blotting elements 12, 12' is centrally provided with an opening, and in addition cushions 13, 13' may be provided with radially extending channels (covered by the said blotting paper), for the purpose of stabilizing the position of the blotting paper. Said opening is connected to a vacuum channel through arms 11, 11' and tubes 9, which channel is connected to a vacuum pump (not shown) in the rear compartment 4 of device 1.

The front portions of arms 11, 11', and thus blotting elements 12, 12', can be moved apart against the action of an adjustable spring 11A, located between the rear portions of the arms 11, 11' and urging these rear portions apart. Said movement is effected by an actuator abutting (the right-hand side of) the rear portion of the (right) arm 11', e.g. a pneumatic actuator 11B which is known per se and which is connected to a pneumatic pipe 14 shown in FIG. 3. The spring 11A can be adjusted by an adjusting screw 11C in (the left-hand side of) the rear portion of the (left) arm 11. Further, any movements of the right arm 11' are transmitted instantly and symmetrically to the left arm 11 by a two-armed lever 11D, which is pivotally connected to the cross beam 10 and to both arms 11, 11'.

By allowing air to escape from the actuator 11B through an adjustable vent (ex Festo; not shown), the blotting elements 12, 12' can be moved together again in a controlled manner under the influence of said spring. The pressure at which the blotting takes place can be adjusted by the said spring, whereas the speed of the blotting elements can be adjusted by both the spring and the said vent.

Present in the front part of environmental chamber 2, extending parallel to tubes 9, is a tube 15 which can be shot downwards at great speed by e.g. a pneumatic actuator and which can subsequently be moved (relatively slowly) upwards again by a stepper motor. Mounted on the end of said tube 15 is an (indirect) holder for a grid, which holder consists of a clamp 15' for tweezers 16 in this embodiment.

Furthermore, a triangular element 17 is connected to tubes 9, which comprises an annular guide 18 at its vertex for guiding tweezers 16, clamp 15' and tube 15.

Disposed beside and under tweezers 16 is a holder for a container or vial 20 for a suspension of particles to be examined. Furthermore, a reservoir (shown without its outer wall) is disposed under the environmental chamber 2, in which reservoir an ultrasonic air humidifier 21 is present, which air humidifier extends through the bottom plate of the environmental chamber 2. Present on the upper side of said 5 reservoir is a cover 22, which catches (overly) large drops from the air humidifier 21. The environmental chamber 2 furthermore contains heating and/or cooling elements (not shown), such as respectively resistive heaters and/or Peltier elements, by which the temperature can be controlled.

The entire preparation of a specimen for a cryoelectron microscope can take place in an automated manner, for example under the control of a PC, providing control signals to any or all of the actuators, heating elements, cooling elements, etc. Following the placement of vial 20, in which a suspension of particles to be examined, and prepared in a manner known in itself, is present, and a period of rest of 20-30 minutes, for example, during which said vial 20 and said suspension can acclimatize, the tweezers 16, in the lower side of whose jaws a grid (ex Stork Veco; not shown) is clamped, is moved down and immersed in the aforesaid suspension. Instead of said immersion, it is also possible to apply a small amount of suspension to one side, e.g. by a pipette or a spraying device. To this end, one side wall of the environmental chamber 2 may be provided with an airlock 25 (FIG. 1).

After the suspension has been applied, tweezers 16 are moved up to a position in which the blotting elements 12, 12, can be pressed against the end of tweezers 16, and thus against the grid. Depending on the circumstances, such as the characteristics of the specific grid, the viscosity of the suspension being used and the temperature, the blotting operation can be repeated one or more times, while it is furthermore possible to adjust the pressure at which said blotting takes place. In addition, it is possible to regulate the thickness of the film in the grid openings in this manner.

Each of the blotting elements 12, 12' has a circular, upright edge 23 on its rear side, which edge is concentric with the rest of the blotting element 12 and which is provided with teeth, sixteen teeth for example. The aforesaid arms 11, 11' each include a plate-shaped body 24, on the end of which a resilient cam is present, which presses against one of the aforesaid teeth upon return movement of the respective arm 11, as a result of which blotting element 12 is moved 1/16th turn. The moment arm 11 moves inwards again, said cam will fall behind the next tooth, so that it is ensured that each time blotting takes place, the blotting element 13 is turned a predetermined distance and is thus provided with an unused piece of blotting paper near the grid. After blotting has been carried out to a sufficient degree, a waiting period may follow so as to allow the above-described draining process in the grid to take place.

In principle, the specimen is now finished and can be dropped or shot into the ethane under the environmental chamber 2 or, alternatively, onto a cooled solid object, such as a copper block placed in a liquid coolant, such as liquid nitrogen or helium (so-called slam-freezing). To this end, vessel 5 is moved upwards to a position close to the bottom plate of environmental chamber 2. Then holder 19 for vial 20, which also functions as a valve, is swung aside by e.g. a pneumatic actuator, of which only a pneumatic pipe 141 is shown in FIG. 3, so that an opening disposed thereunder is released and the tweezers 16 with the tube 15 are shot downwards. The sample that is present in the grid will vitrify almost instantaneously, after which it can be moved to the aforesaid annular channel in vessel 5 or be stored in another manner. Then another sterile grid can be placed in tweezers 16 and the tweezers 16 are moved upwards by a stepper motor, after which the next specimen can be made.

The invention and the above-described embodiments enable the preparation of a large number of specimens for a cryo-electron microscope in a reproducible manner and within a (relatively) short time. Since the main blotting parameters, such as pressure, speed, duration, blotting medium, and/or the number of blotting cycles, are controllable and blotting does not lead to a disturbance of the environment in environmental chamber 2, the burden on the specimen, which is at its most vulnerable state during said blotting and the subsequent drainage, is minimized. Further, the said parameters each individually can be optimized for a particular (type of) sample.

The use of an air humidity level of more than 97%, preferably 100%, further enhances this effect. Although existing devices for preparing specimens use high air humidity levels, it has become apparent that it is possible, by using sensors capable of detecting an air humidity level of 97% or higher and/or by checking for the presence of mist and/or condensation on the walls of the environmental chamber, to adjust an air humidity level of 100% without large drops being formed, which might interfere with the specimen preparation process.

Examples of the above-mentioned actuators to operate the components in the environmental chamber are inter alia pneumatic actuators, stepper motors, and linear motors.

The invention is not restricted to the above-described embodiments, of course, which can be varied in several ways without departing from the scope of the invention as defined in the claims. For example, the environmental chamber can be filled with other gasses instead of or in addition to air. Also, if a medium other than water is used for suspending the particles to be examined, the gas in the environmental chamber will preferably not be saturated with water but with said medium.

The invention claimed is:

1. A device for preparing specimens for a cryoelectron microscope, comprising:
   an environmental chamber;
   a holder for a sample or a carrier;
   at least one blotting element having a medium for absorbing liquid disposed in the environmental chamber;
   a control unit;
   at least one driving mechanism operably coupled to the control unit and coupled to the at least one blotting element;
   wherein the control unit is configured to control the movement of said blotting element towards the sample or carrier in a controlled manner to adjust the pressure with which the blotting element is pressed against the sample or carrier; and
   a cooling medium configured for cooling down said sample or carrier.

2. The device of claim 1, wherein the speed with which the blotting element is moved towards the sample or carrier is adjustable by the at least one driving mechanism.

3. The device of claim 1, wherein one blotting element is provided on each side of the sample or carrier.

4. The device of claim 1, wherein the blotting element is adapted to move automatically after a blotting cycle to expose an unused portion of the blotting element.

5. The device of claim 1, wherein the blotting element comprises a pad or cushion to which the medium for absorbing liquid is or can be attached.

6. The device of claim 3, wherein the blotting elements are mounted obliquely with respect to one another.

7. The device of claim 1, and further comprising a cooling element disposed inside the environmental chamber.

8. The device of claim 3, wherein the driving mechanism comprises an actuator cooperating with a spring and wherein the actuator and the spring are arranged to control the movements of the blotting elements so as to blot the sample or carrier one or more times at a predetermined pressure.

9. The device of claim 8, wherein the driving mechanism is arranged to control the speed of at least some of the movements of the blotting elements.

10. A device for preparing specimens for a cryoelectron microscope, comprising:
    an environmental chamber;
    a holder for a sample or a carrier;
    at least one blotting element having a medium for absorbing liquid disposed in the environmental chamber;
    a control unit;
    at least one driving mechanism operably coupled to the control unit and coupled to the at least one blotting element;
    wherein the control unit is configured to control the movement of said blotting element towards the sample or carrier in a controlled manner to adjust the speed with which the blotting element is pressed against the sample or carrier; and
    a cooling medium configured for cooling down said sample or carrier.

11. The device of claim 10, wherein one blotting element is provided on each side of the sample or carrier.

12. The device of claim 10, wherein the blotting element is adapted to move automatically after a blotting cycle to expose an unused portion of the blotting element.

13. The device of claim 10, wherein the blotting element comprises a pad or cushion to which the medium for absorbing liquid is or can be attached.

14. The device of claim 11, wherein the blotting elements are mounted obliquely with respect to one another.

15. The device of claim 10, and further comprising a cooling element disposed inside the environmental chamber.

16. The device of claim 10 the driving mechanism comprises an actuator cooperating with a spring wherein the actuator and the spring are arranged to control the movements of the blotting elements so as to blot the sample or carrier one or more times at a predetermined speed.

17. A device for preparing specimens for a cryoelectron microscope, comprising:
    an environmental chamber;
    a holder for a sample or a carrier;

at least one blotting element having a medium for absorbing liquid disposed in the environmental chamber;

a control unit;

moving means operably coupled to the control unit and coupled to the at least one blotting element;

wherein said control unit is configured to control the movement of said at least one blotting element towards the sample or carrier in a controlled manner to adjust the pressure with which at least one blotting element is pressed against the sample or carrier, or to adjust the speed with which said at least one blotting element is moved towards the sample or carrier; and a cooling medium configured for cooling down said sample or carrier.

18. The device of claim 17, wherein said moving means comprises a spring and an actuator coupled to the spring.

19. The device of claim 18, wherein one blotting element is provided on each side of the sample or carrier, and the spring is operatively coupled to each blotting element.

20. The device of claim 19, wherein each blotting element is adapted to move automatically after a blotting cycle to expose an unused portion of the blotting element.

21. The device of claim 20, wherein the blotting elements are mounted obliquely with respect to one another.

22. The device of claim 21, wherein each blotting element comprises a pad or cushion to which the medium for absorbing liquid is or can be attached.

* * * * *